US006086895A

United States Patent [19]
Höök et al.

[11] Patent Number: 6,086,895
[45] Date of Patent: *Jul. 11, 2000

[54] FIBRONECTIN BINDING PROTEIN

[75] Inventors: Magnus Höök, Birmingham, Ala.; Kjell Martin Lindberg, Uppsala, Sweden; Per-Eric Lindgren, Uppsala, Sweden; Lars Christer Signäs, Uppsala, Sweden

[73] Assignee: Alfa Laval Agri International, Sweden

[*] Notice: This patent is subject to a terminal disclaimer.

[21] Appl. No.: 08/904,179

[22] Filed: Aug. 1, 1997

Related U.S. Application Data

[60] Continuation of application No. 08/428,713, Apr. 25, 1995, Pat. No. 5,866,541, which is a division of application No. 08/125,222, Sep. 23, 1993, Pat. No. 5,416,021, which is a continuation of application No. 07/973,551, Nov. 9, 1992, abandoned, which is a continuation of application No. 07/352,949, May 17, 1989, abandoned.

Foreign Application Priority Data

May 20, 1998 [SE] Sweden .................... 8801894

[51] Int. Cl.[7] .................. A61K 39/085; A61K 39/09; A61K 38/00; C07K 17/00
[52] U.S. Cl. .................. 424/243.1; 424/184.1; 424/190.1; 424/237.1; 514/2; 514/12; 530/324; 530/350
[58] Field of Search .................. 530/324, 350; 514/2, 12; 424/184.1, 190.1, 237.1, 243.1

[56] References Cited

U.S. PATENT DOCUMENTS

| | | | |
|---|---|---|---|
| 3,917,818 | 11/1975 | Botes | 424/87 |
| 4,312,942 | 1/1982 | Blobel et al. | 435/7.24 |
| 4,425,330 | 1/1984 | Norcross et al. | 424/92 |
| 4,645,757 | 2/1987 | Hjerten et al. | 514/54 |
| 4,784,989 | 11/1988 | Hook et al. | 514/21 |
| 4,795,803 | 1/1989 | Lindberg et al. | 530/324 |
| 5,189,015 | 2/1993 | Hook et al. | 514/2 |
| 5,320,951 | 6/1994 | Höök et al. | |
| 5,416,021 | 5/1995 | Höök et al. | |
| 5,440,014 | 8/1995 | Höök et al. | |
| 5,571,514 | 11/1996 | Höök et al. | |
| 5,648,240 | 7/1997 | Höök et al. | |
| 5,652,217 | 7/1997 | Höök et al. | |
| 5,725,804 | 3/1998 | Yen . | |
| 5,770,702 | 6/1998 | Hook et al. | |
| 5,789,549 | 8/1998 | Höök et al. | |
| 5,840,846 | 11/1998 | Höök et al. | |
| 5,866,541 | 2/1999 | Höök et al. | |
| 5,910,441 | 6/1999 | Rocha et al. | |

FOREIGN PATENT DOCUMENTS

| | | |
|---|---|---|
| 0163623 | 12/1985 | European Pat. Off. . |
| 0294349 | 12/1988 | European Pat. Off. . |
| 0342173 | 11/1989 | European Pat. Off. . |
| 0343137 | 11/1989 | European Pat. Off. . |
| 0397633 | 11/1990 | European Pat. Off. . |
| 87/02272-9 | 6/1987 | Sweden . |
| 88/01894-0 | 5/1988 | Sweden . |
| 89/01687-7 | 5/1989 | Sweden . |
| WO-85/05037 | 11/1985 | WIPO . |
| WO-A1-85/05553 | 12/1985 | WIPO . |
| WO 92/02555 | 2/1992 | WIPO . |

OTHER PUBLICATIONS

Abrahmsen et al.—*Nucl. Acid Res.* 14(18):7487–7500 (1986).
Chhatwal et al.—*Comp. Immunol. Microbiol. Infect. Dis.* 10(2):99–108 Abstract (1987).
Duggleby et al.—*Nuc. Acid. Res.* 11(10):3065–3076 (1983).
Espersen et al.—*Infect. and Immun.* 37(2):526–531 (Aug. 1982).
Flock et al.—*EMBO J.* 6(8):2351–2357 (1987).
Froman et al.—*J. Biol. Chem.* 262(14):6564–6571 (1987).
Keil–Dlouha et al. —*Biochem. Biophys. Acta.* 727:115–21 (1983).
Lofdahl et al.—*Proc. Natl. Acad. Sci.* 80:697–701 (Feb. 1983).
Mamo et al.—*Micro. Pathog.* 2(6):417–424 Abstract (1987).
McGavin et al.—*J. Biol. Chem.* 266(13):8343–7 (1991).
Myhre et al.—*J. Med. Microbiol.* 18(2):189–196 Abstract (1984).
Myhre—*Infect. Immun.* 40(1):29–34 (1983).
Nuesch et al.—*Gene* 32:243–249 (1984).
Overbeeke et al.—*J. Mol. Biol.* 163:513–532 (1983).
Raja et al.—*Infect. Immun.* 58(8):2593–8 (1990).
Ryden et al.—*J. Biol. Chem.* 258(5):3396–3401 (Mar. 1983).
Sambrook et al.—*Molecular Cloning: a Laboratory Manuel*, (2d), 6.39–6.43, B.9 (1989).
Signas et al.—*Proc. Natl. Acad. Sci.* 86:699–703 (1989).
Switalski et al.—*Eur. J. Clin. Microbiol.* 1:381–387 (1982).

*Primary Examiner*—Nita Minnifield
*Attorney, Agent, or Firm*—Burns, Doane, Swecker, & Mathis, L.L.P.

[57] ABSTRACT

The present invention relates to new recombinant DNA-molecules comprising nucleotide sequences of *S. dygalactiae* encoding for at least one protein or polypeptide having fibronectin binding property.

6 Claims, 9 Drawing Sheets

FIG. 3A

```
pSDF102
A1  EDTQTSQEDI  V-LGGPGQVI  DFTEDSQPGM  SGNNSHTT
    ||   ||||   |  || ||||  ||||| | ||  || ||||
A2  EDSKPSQEDE  VIIGGQGQVI  DFTEDTQSGM  SGDNSHTDG TVLE
    ||||||||||  ||||||||||  |||||| ||  || 
A3  EDSKPSQEDE  VIIGGQGQVI  DFTEDTQTGM  SGAGQVESP
     |  ||||    |  |  |||   || ||         |
    TITEETHKPE  IIMGGQSDPI  DMVEDTLPGM  SGSNEAEDT
```

FIG. 3B

```
pSDF203
A1  EETLPTEQGQ  SGSTTEVEDT  KGPEVIIGGQ  GEIVDI
    || |||||||  ||||||||||  ||||||||||  || |||
A2  EENLPTEQGQ  SGSTTEVEDT  KGPEVIIGGQ  GEVVDI
    || |||||||  |||||||||    |           |
A3  EESLPTEQGQ  SGSTTEVEDS  KPKLSIHFDN  EWPKED
```

FIG. 4

```
1   ----------+-- --------+---- -----+------ ---+--------  48
    CTAGATACCTCA GAAAACAAAAAA TCTGTAACTGAA AAAGTAATAACT
    LeuAspThrSer GluAsnLysLys SerValThrGlu LysValIleThr
49  -+---------+ ---------+-- -------+---- -----+------  96
    AGCGATGTTAAA TATAAGATTAAT GATAAAGAAGTG AAAGGTAAAGAA
    SerAspValLys TyrLysIleAsn AspLysGluVal LysGlyLysGlu
97  ---+-------- -+---------+ ----------+-- -------+----  144
    CTAGACGATGTC TCTTTAACTTAC AGTAAAGAAACC GTTCGTAAGCCA
    LeuAspAspVal SerLeuThrTyr SerLysGluThr ValArgLysPro
145 -----+------ ---+-------- -+---------+ ----------+--  192
    CAGGTGGAACCA AATGTTCCTGAT ACACCTCAGGAA AAACCATTGACA
    GlnValGluPro AsnValProAsp ThrProGlnGlu LysProLeuThr
193 --------+---- -----+------ ---+-------- -+---------+  240
    CCGCTTGCACCG TCAGAACCTTCA CAACCATCTATT CCAGAGACACCA
    ProLeuAlaPro SerGluProSer GlnProSerIle ProGluThrPro
241 ----------+-- --------+---- -----+------ ---+--------  288
    CTGATACCGTCA GAACCTTCAGTT CCAGAGACATCA ACACCAGAAGGT
    LeuIleProSer GluProSerVal ProGluThrSer ThrProGluGly
289 -+---------+ ---------+-- --------+---- -----+------  336
    CCAACAGAGGGA GAAAATAATCTT GGTGGTCAGAGT GAAGAGATAACG
    ProThrGluGly GluAsnAsnLeu GlyGlyGlnSer GluGluIleThr
337 ---+-------- -+---------+ ----------+-- --------+----  384
    ATTACAGAAGAT TCTCAATCAGGG ATGTCTGGTCAA AATCCTGGTTCT
    IleThrGluAsp SerGlnSerGly MetSerGlyGln AsnProGlySer
385 -----+------ ---+-------- -+---------+ ----------+--  432
    GGAAATGAAACA GTGGTTGAAGAC ACTCAAACAAGT CAAGAGGATATT
    GlyAsnGluThr ValValGluAsp ThrGlnThrSer GlnGluAspIle
433 --------+---- -----+------ ---+-------- -+---------+  480
    GTACTTGGTGGT CCAGGTCAAGTG ATTGACTTTACA GAAGATAGCCAA
    ValLeuGlyGly ProGlyGlnVal IleAspPheThr GluAspSerGln
481 ----------+-- --------+---- -----+------ ---+--------  528
    CCGGGTATGTCT GGTAATAATAGC CATACTATTACA GAAGATTCTAAA
    ProGlyMetSer GlyAsnAsnSer HisThrIleThr GluAspSerLys
529 -+---------+ ---------+-- -------+---- -----+------  576
    CCAAGTCAAGAG GATGAGGTGATA ATCGGCGGTCAA GGTCAGGTGATT
    ProSerGlnGlu AspGluValIle IleGlyGlyGln GlyGlnValIle
577 ---+-------- -+---------+ ----------+-- --------+----  624
    GACTTTACAGAA GATACTCAATCT GGTATGTCTGGG GATAATAGCCAT
    AspPheThrGlu AspThrGlnSer GlyMetSerGly AspAsnSerHis
625 -----+------ ---+-------- -+---------+ ----------+--  672
    ACAGATGGGACA GTGCTTGAAGAA GACTCTAAACCA AGTCAAGAGGAT
    ThrAspGlyThr ValLeuGluGlu AspSerLysPro SerGlnGluAsp
673 --------+---- -----+------ ---+-------- -+---------+  720
    GAGGTGATAATC GGCGGTCAAGGT CAAGTGATTGAC TTTACAGAAGAT
    GluValIleIle GlyGlyGlnGly GlnValIleAsp PheThrGluAsp
```

FIG. 4

```
721  ----------+--  -------+----  -----+------  ---+---------  768
     ACCCAAACCGGT  ATGTCTGGGGCT  GGACAAGTAGAG  AGTCCAACAATC
     ThrGlnThrGly  MetSerGlyAla  GlyGlnValGlu  SerProThrIle
769  -+---------+  ---------+--  --------+----  -----+------  816
     ACCGAAGAAACC  CATAAACCAGAA  ATAATCATGGGC  GGTCAAAGTGAC
     ThrGluGluThr  HisLysProGlu  IleIleMetGly  GlyGlnSerAsp
817  ---+--------  -+---------+  ----------+--  --------+----  864
     CCTATTGATATG  GTTGAGGACACT  CTTCCTGGTATG  TCTGGCTCTAAT
     ProIleAspMet  ValGluAspThr  LeuProGlyMet  SerGlySerAsn
865  -----+------  ----+--------  -+---------+  ----------+--  912
     GAAGCTACTGTT  GTGGAAGAAGAC  ACACGTCCTAAA  CTTCAATTCCAT
     GluAlaThrVal  ValGluGluAsp  ThrArgProLys  LeuGlnPheHis
913  --------+----  -----+------  ---+--------  -+---------+  960
     TTTGATAATGAA  GAGCCCGTTCCT  GCAACGGTTCCA  ACCGTTTCTCAA
     PheAspAsnGlu  GluProValPro  AlaThrValPro  ThrValSerGln
961  ----------+--  --------+----  -----+------  ---+---------  1008
     ACTCCTATTGCT  CAGGTAGAAAGT  AAAGTGCCTCAT  GCCAAAGCAGAG
     ThrProIleAla  GlnValGluSer  LysValProHis  AlaLysAlaGlu
1009 -+---------+  ----------+--  --------+----  -----+------  1056
     AGTGCGTTACCT  CAAACTGGAGAT  ACAAATAAACTA  GAAACGTTCTTT
     SerAlaLeuPro  GlnThrGlyAsp  ThrAsnLysLeu  GluThrPhePhe
1057 ---+--------  -+---------+  ----------+--  --------+----  1104
     ACCATTACAGCA  CTAACTGTTATT  GGAGCGGCAGGA  TTACTAGGCAAA
     ThrIleThrAla  LeuThrValIle  GlyAlaAlaGly  LeuLeuGlyLys
1105 -----+------  ---+--------  -+---------+  ----------+--  1152
     AAACGTCGTAAT  AATCAAACTGAT  TAATCAGCAGAT  TTCATCAAACGC
     LysArgArgAsn  AsnGlnThrAsp  EndSerAlaAsp  PheIleLysArg
1153 --------+----  -----+------  ---+--------  -+---------+  1200
     TATAAACAAGGC  TAACATTTTAGC  CTTGTTTTATAT  TGTTTCACTGAC
     TyrLysGlnGly  End
1201 ----------+--  --------+----  -----+------  ---+---------  1248
     CTCTAAAAGTTA  TGACTGTTTTAA  AGGGGGGGTAGG  CCAATCCTCAAA
1249 -+---------+  ----------+--  --------+----  -----+------  1296
     AGTAGTTAAGTT  GAGAAACACCAC  ATCACTTTAGTC  TTACTGCGCATA
1297 ---+--------  -+---------+  ----------+--  --------+----  1344
     CTAAAAGCAAAA  GATAATTAGGAG  CACTTGCTAACT  GGAAAAAATCAA
1345 -----+------  ---+--------  -+---- 1374
     ATGCAAAGCTAG  TTGCCAAAGAAC  TCTAGA
```

FIG. 5

```
1   ---------+--  -------+----  -----+------  ---+--------  48
    CTCGAGGAAACT  TTGCCAACAGAG  GAACATCAATCA  GGTGATACCACA
    LeuGluGluThr  LeuProThrGlu  GluHisGlnSer  GlyAspThrThr
49  -+---------+  ----------+--  --------+----  -----+------  96
    ACTATTGAAGAT  ACTCGCCCGATT  GATACCATGTCA  GGTCTATCAGGA
    ThrIleGluAsp  ThrArgProIle  AspThrMetSer  GlyLeuSerGly
97  ---+--------  -+---------+  ----------+--  --------+----  144
    GAGACTGGGCAG  TCTGGTAATACT  ACAATTGAGGAA  GATAGTACGACT
    GluThrGlyGln  SerGlyAsnThr  ThrIleGluGlu  AspSerThrThr
145 -----+------  ---+--------  -+---------+  ----------+--  192
    CACGTTAAATTC  TCAAAACGTGAT  ATTAATGGTAAA  GAACTAGCAGGT
    HisValLysPhe  SerLysArgAsp  IleAsnGlyLys  GluLeuAlaGly
193 --------+----  -----+------  ---+--------  -+---------+  240
    GCTATGATTGAA  CTACGTAATCTA  TCAGGTCAAACT  ATTCAATCATGG
    AlaMetIleGlu  LeuArgAsnLeu  SerGlyGlnThr  IleGlnSerTrp
241 ----------+--  --------+----  -----+------  ---+--------  288
    ATATCAGACGGC  ACAGTTAAAGTT  TTCTACTTGATG  CCAGGGACTTAT
    IleSerAspGly  ThrValLysVal  PheTyrLeuMet  ProGlyThrTyr
289 -+---------+  ----------+--  --------+----  -----+------  336
    CAATTTGTGGAG  ACGGCAGCGCCA  GAAGGTTATGAA  TTGGCAGCTCCA
    GlnPheValGlu  ThrAlaAlaPro  GluGlyTyrGlu  LeuAlaAlaPro
337 ---+--------  -+---------+  ----------+--  --------+----  384
    ATTACCTTCACA  ATTGATGAGAAA  GGACAAATTTGG  GTAGACAGTACA
    IleThrPheThr  IleAspGluLys  GlyGlnIleTrp  ValAspSerThr
433 --------+----  -----+------  ---+--------  -+---------+  480
    ATTACTGAGGCG  AGTCAATCTATT  GATTTCGAGGAA  ACTTTACCAACT
    IleThrGluAla  SerGlnSerIle  AspPheGluGlu  ThrLeuProThr
481 ----------+--  --------+----  -----+------  ---+--------  528
    GAACAAGGCCAA  TCTGGCTCTACA  ACGGAGGTTGAG  GATACTAAAGGC
    GluGlnGlyGln  SerGlySerThr  ThrGluValGlu  AspThrLysGly
529 -+---------+  ----------+--  --------+----  -----+------  576
    CCAGAAGTCATT  ATCGGCGGTCAG  GGAGAGATTGTT  GATATCGAGGAG
    ProGluValIle  IleGlyGlyGln  GlyGluIleVal  AspIleGluGlu
577 ---+--------  -+---------+  ----------+--  --------+----  624
    AACTTACCAACT  GAACAAGGCCAA  TCTGGCTCTACA  ACTGAAGTAGAG
    AsnLeuProThr  GluGlnGlyGln  SerGlySerThr  ThrGluValGlu
625 -----+------  ---+--------  -+---------+  ----------+--  672
    GATACTAAAGGC  CCAGAAGTCATT  ATCGGCGGTCAA  GGAGAGGTTGTT
    AspThrLysGly  ProGluValIle  IleGlyGlyGln  GlyGluValVal
673 --------+----  -----+------  ---+--------  -+---------+  720
    GATATTGAGGAG  AGCTTACCAACT  GAACAAGGCCAA  TCTGGCTCTACA
    AspIleGluGlu  SerLeuProThr  GluGlnGlyGln  SerGlySerThr
721 ----------+--  --------+----  -----+------  ---+--------  768
    ACTGAAGTAGAA  GATAGCAAGCCT  AAACTCTCTATC  CACTTTGATAAC
    ThrGluValGlu  AspSerLysPro  LysLeuSerIle  HisPheAspAsn
```

FIG. 5

```
769 -+---------+  ---------+--  -------+----  -----+------ 816
    GAGTGGCCTAAG GAAGACAAACCA CAACTACCTGCC GTTGAAAAACCT
    GluTrpProLys GluAspLysPro GlnLeuProAla ValGluLysPro
817 ---+--------  -+---------+  ---------+--  -------+---- 864
    AAGACTAAGGAG AGCTTGCCAGCC GCAGGGGAAGCT GAACATGTCTTA
    LysThrLysGlu SerLeuProAla AlaGlyGluAls GluHisValLeu
865 -----+------  ---+-------- 888
    TCTACTATCGTG GGAGCAATGATC
    SerThrIleVal GlyAlaMetIle
```

FIBRONECTIN BINDING PROTEIN

This application is a continuation of application Ser. No. 08/428,713, filed Apr. 25, 1995 U.S. Pat. No. 5,866,541, which is a divisional of application Ser. No. 08/125,222, filed Sep. 23, 1993 U.S. Pat. No. 5,416,021 which is a continuation of application Ser. No. 07/973,551, filed Nov. 9, 1992 now abandoned, which is a continuation of application Ser. No. 07/352,949, filed May 17, 1989 now abandoned.

DESCRIPTION

1. Technical Field

The present invention relates to fibronectin binding proteins and hybrid-DNA molecules, e.g., plasmids or phages containing at least one nucleotide sequence encoding for said proteins. Further the invention relates to microorganisms containing such molecules and their use to produce said proteins, and the synthetic production of said proteins.

The object of the present invention is to obtain minimal fibronectin binding proteins.

A further object of the present invention is to obtain said proteins by means of genetic engineering technique using e.g., a plasmid containing a nucleotide sequence encoding for the proteins.

A further object of the present invention is to obtain a possibility to prepare said proteins by means of chemical synthesis.

2. Background of the Invention

WO-A1-85/05553 discloses bacterial cell surface proteins having fibronectin, fibrinogen, collagen, and/or laminin binding ability. Thereby it is shown that different bacteria have an ability to bind to fibronectin, fibrinogen, collagen and/or laminin. It is further shown that fibronectin binding protein from *Staphylococcus aureus* has a molecular weight of 165 kD, and/or 87 kD, whereby it is probable that the smaller protein is a part of the larger one.

Fibronectin is a large glycoprotein having a molecular weight of about 450 kD and having two similar subunits, which can have varying molecular sizes depending on a complex splicing pattern of the precursor mRNA. The protein is present in basement membranes, and connective tissue, but also in a soluble form in different body fluids, such as blood plasma (1). After the original discovery by Kuusela in 1978 that *S. aureus* binds to fibronectin (2) it has been shown that certain strains of other pathogenic bacteria, such as streptococci of different serological types (3), *E. coli* (4) and Salmonella (5) can bind to this protein (6).

Adhesion of pathogenic bacteria to surfaces is today a generally recognized concept in the discussions of wound pathogens using surface receptors to bind to different proteins on epithelium cell surfaces, in connective tissue matrix, and in wound crusts, such as e.g., fibronectin, fibrinogen, collagen and laminin. The problem is that these receptors are present in a relatively small amount on the bacterial cell surface, and that they are difficult to release. One feasible way in cases the receptors consist of proteins is to clone the genes for the receptors in question to be able to prepare them in quantities which makes it considerably easier to study infections and the course of infections as well as prophylactical and therapeutical treatment of infections by wound pathogens.

Screening studies of different serological groups of streptococci, such as A, C, and G according to Lancefield (3) have shown that the strains tested can bind to different connective tissue proteins such as fibronectin, fibrinogen, collagen and laminin and different immunoglobulins (7,8) to a varying degree and with different specificity.

In order to further characterize fibronectin binding proteins from streptococci, particularly genes from *Streptococcus dysgalactiae* for such proteins have been cloned in *E. coli*. The fibronectin binding domains of these proteins have also been localized and properties and functions of proteins containing these domains will be discussed below.

DESCRIPTION OF THE PRESENT INVENTION

It has now surprisingly been shown possible to obtain hybrid-DNA molecules comprising nucleotide sequences of the genes coding for proteins or polypeptides having fibronectin binding properties. As evident from the below the following nucleotide sequences [SEQ ID NOS.:1 & 2] are present in the plasmides, pSDF102, and pSDF203, respectively, which encode said proteins.

```
CTA GAT ACC TCA GAA AAC AAA AAA TCT GTA ACT GAA AAA GTA ATA ACT

AGC GAT GTT AAA TAT AAG ATT AAT GAT AAA GAA GTG AAA GGT AAA GAA

CTA GAC GAT GTC TCT TTA ACT TAC AGT AAA GAA ACC GTT CGT AAG CCA

CAG GTG GAA CCA AAT GTT CCT GAT ACA CCT CAG GAA AAA CCA TTG ACA

CCG CTT GCA CCG TCA GAA CCT TCA CAA CCA TCT ATT CCA GAG ACA CCA

CTG ATA CCG TCA GAA CCT TCA GTT CCA GAG ACA TCA ACA CCA GAA GGT

CCA ACA GAG GGA GAA AAT AAT CTT GGT GGT CAG AGT GAA ATA ACG ATT

ACA GAA GAT TCT CAA TCA GGG ATG TCT GGT CAA AAT CCT GGT TCT GGA

AAT GAA ACA GTG GTT

GAA GAC ACT CAA ACA AGT CAA GAG GAT ATT GTA CTT GGT GGT CCA GGT

CAA GTG ATT GAC TTT ACA GAA GAT AGC CAA CCG GGT ATG TCT GGT AAT

AAT AGC CAT ACT ATT ACA

GAA GAT TCT AAA CCA AGT CAA GAG GAT GAG GTG ATA ATC GGC GGT CAA
```

```
                           -continued
GGT CAG GTG ATT GAC TTT ACA GAA GAT ACT CAA TCT GGT ATG TCT GGG

GAT AAT AGC CAT ACA GAT GGG ACA GTG CTT GAA

GAA GAC TCT AAA CCA AGT CAA GAG GAT GAG GTG ATA ATC GGC GGT CAA

GGT CAA GTG ATT GAC TTT ACA GAA GAT ACC CAA ACC GGT ATG TCT GGG

GCT GGA CAA GTA GAG AGT CCA ACA ACT ACC GAA GAA ACC CAT AAA CCA

GAA ATA ATC ATG GGC GGT CAA AGT GAC CCT ATT GAT ATG GTT GAG GAC

ACT CTT CCT GGT ATG TCT GGC TCT AAT GAA GCT ACT GTT GTG GAA GAA

GAC ACA CGT CCT AAA CTT CAA TTC CAT TTT GAT AAT GAA GAG CCC GTT

CCT GCA ACG GTT CCA ACC GTT TCT CAA ACT CCT ATT GCT CAG GTA GAA

AGT AAA GTG CCT CAT GCC AAA GCA GAG AGT GCG TTA CCT CAA ACT GGA

GAT ACA AAT AAA CTA GAA ACG TTC TTT ACC ATT ACA GCA CTA ACT GTT

ATT GGA GCG GCA GGA TTA CTA GGC AAA AAA CGT CGT AAT AAT CAA ACT

GAT TAA TCA GCA GAT TTC ATC AAA CGC TAT AAA CAA GGC TAA CAT TTT

AGC CTT GTT TTA TAT TGT TTC ACT GAC CTC TAA AAG TTA TGA CTG TTT

TAA AGG GGG GGT AGG CCA ATC CTC AAA AGT AGT TAA GTT GAG AAA CAC

CAC ATC ACT TTA GTC TTA CTG CGC ATA CTA AAA GCA AAA GAT AAT TAG

GAG CAG TTG CTA ACT GGA AAA AAT CAA ATG CAA AGC TAG TTG CCA AAG

AAC TCT AGA and/or

CTC GAG GAA ACT TTG CCA AAC GAG GAA CAT CAA TCA GGT GAT ACC ACA

ACT ATT GAA GAT ACT CGC CCG ATT GAT ACC ATG TCA GGT CTA TCA GGA

GAG ACT GGG CAG TCT GGT AAT ACT ACA ATT GAG GAA GAT AGT ACG ACT

CAC GTT AAA TTC TCA AAA CGT GAT ATT AAT GGT AAA GAA CTA GCA GGT

GCT ATG ATT GAA CTA CGT AAT CTA TCA GGT CAA ACT ATT CAA TCA TGG

ATA TCA GAC GGC ACA GTT AAA GTT TTC TAC TTG ATG CCA GGG ACT TAT

CAA TTT GTG GAG ACG GCA GCG CCA GAA GGT TAT GAA TTG GCA GCT CCA

ATT ACC TTC ACA ATT GAT GAG AAA GGA CAA ATT TGG GTA GAC AGT ACA

ATT ACT GAG GCG AGT CAA TCT ATT GAT TTC

GAG GAA ACT TTA CCA ACT GAA CAA GGC CAA TCT GGC TCT ACA ACG GAG

GTT GAG GAT ACT AAA GGC CCA GAA GTC ATT ATC GGC GGT CAG GGA GAG

ATT GTT GAT ATC

GAG GAG AAC TTA CCA ACT GAA CAA GGC CAA TCT GGC TCT ACA ACT GAA

GTA GAG GAT ACT AAA GGC CCA GAA GTC ATT ATC GGC GGT CAA GGA GAG

GTT GTT GAT ATT

GAG GAG AGC TTA CCA ACT GAA CAA GGC CAA TCT GGC TCT ACA ACT GAA

GTA GAA GAT

AGC AAG CCT AAA CTC TCT ATC CAC TTT GAT AAC GAG TGG CCT AAG GAA

GAC AAA CCA CAA CTA CCT GCC GTT GAA AAA CCT AAG ACT AAG GAG AGC

TTG CCA GCC GCA GGG GAA GCT GAA CAT GTC TTA TCT ACT ATC GTG GGA

GCA ATG ATC
``` whereby the smaller repetitive regions (cf. FIG. 3) in each gene above code for the peptides having fibronectin binding activity.

The invention further comprises a plasmid or phage comprising a nucleotide sequence coding for said fibronectin binding proteins.

The invention further comprises micro-organisms containing at least one hybrid-DNA molecule according to above. Such micro-organisms have been deposited at the Deutsche Sammlung von Mikroorganismen under deposition number DSM 4614 (pSDF102) and DSM 4613 (pSDF203).

The invention further relates to a process for preparing fibronectin binding proteins comprising transfer of at least one hybrid-DNA molecule according to above into a micro-organism, cultivating the said micro-organism in a culture medium, and isolating the protein thus formed in a manner known per se.

A further aspect of the present invention comprises a chemical synthesis of the fibronectin binding proteins, whereby amino acids connected into peptides in which the order of amino acids is based upon said nucleotide sequences encoding said proteins. The synthesis starts from the C-terminal glycine, and aspartic acid, respectively, which are reacted stepwise with the appropriate amino acid, whereby they are finally reacted with glutamic acid, and glutamic acid, respectively, at the N-terminal end to the formation of the fibronectin binding peptide regions.

Appropriate amino acids can also be fused to said amino acid sequence such as the IgG binding region of protein A. The invention will be described more in detail in the following with reference to the Examples given, however, without being restricted thereto.

EXAMPLE 1

Construction of a Gene Bank of Chromosomal DNA from *Streptococcus dysgalactiae*

Chromosomal DNA from *Streptococcus dysgalactiae*, strain S2, was prepared in accordance with the perchlorate method (9). The DNA was partially cleaved using Sau 3AI, was size fractionated on a 1% agarose gel, and the DNA fragment within the size range 3 to 9 kb were collected, electro eluated, and purified on a Nensorb (Du Pont) column.

The plasmid vector pUC18 was cleaved using Bam HI and was phosphatase treated. The partially cleaved and fractionated streptococcus-DNA was ligated with the cleaved pUC18 vector. The ligation mixture was transformed to freeze competent *E. coli*, strain TG1, and was spred on LA plates containing ampicillin (50 µg/ml) and IPTG (0.1 mM), and 0.004% X-gal, called axi-plates. White colonies were transferred to LA plates with ampicillin (50 µg/ml).

Screening of a Gene Bank for a Fibronectin Binding Protein (FNBP)

The white colonies from the axi plates were picked using tooth picks to LA plates with ampicillin, 52 colonies per plate. In total 728 transformants were collected. These were screened with regard to fibronectin binding activity using a filter assay method according to below.

Transformants are picked from an axi-plates to LA plates with ampicillin, and the plates are incubated over night. From these plates the colonies are replicated over to new LA plates, and which are incubated at 37° C. over night. A nitro-cellulose filter is put onto each agarplate with grown out colonies. When the filters are completely moistened the colonies are attached by suction and the filters are carefully removed. The filters are exposed to chloroform vapour for 5 min, and are then washed, 3×10 min, 37° C. in a buffer solution consisting of 100 mM Tris-HCl pH 7.5, 0.05% Tween-40, and 150 mM NaCl. The filters are allowed to dry at room temperature for about 30 min. The filters are preincubated in 150 mM NaCl, 10 mM Tris-HCl pH 7.5, and 1.4% fat free milk powder, for 2 hrs at 37° C., or room temperature over night. The milk powder buffer has to be freshly prepared. $^{125}$I labelled fibronectin is added (about 30,000 cpm per filter), and the filters are incubated at room temperature over night. The filters are washed, 3×10 min at 37° C. using a solution of 0.05% Tween-40, and 150 mM NaCl, whereupon the filters are dried. An unexposed film is put thereon, and is exposed for 3 to 5 days. The film is developed and the clones which have bound to $^{125}$I-fibronectin are identified and isolated.

The filter screening assay showed 3 positive clones, which all were further analysed. The fibronectin binding ability was further determined in a competition assay (10). Lysate of the *E. coli* clones were prepared by lysing the bacteria using lysozyme (1 mg/ml) in a buffer solution consisting of 100 mM Tris-HCl pH 7.5, 150 mM NaCl, and 1 mM EDTA. The fibronectin binding acti-vity was analysed by determining the ability of the lysates to compete with *S. aureus*, strain Cowan I (alternatively strain 8325-4), and *S. dysgalactiae*, strain S2, respectively, with regard to their ability to bind to the $^{125}$I-labelled 29 kD fragment of fibronectin. The test showed that it is possible to drive out the fibronectin binding to the two staphylococcal strains, as well as strain S2 of *S. dysgalactiae* when using lysates of *E. coli* clones containing the strepto-cocci DNA. Inversely the binding of the 29 kD fragment of fibronectin to *S. dysgalactiae* can be inhibited by adding a lysate of *E. coli* clone containing a gene for fibronectin binding protein of *S. aureus*.

Restriction Mapping and Subcloning

Plasmid-DNA of the three positive subclones from the filter assay, called pSDF100, pSDF200, and pSDF300 were prepared using the LiCl method (11) and determined to be 4.9 kb, 6.9 kb, and 6.5 kb, respectively, by cleavages using restriction enzymes and analysis on agarose gels. All three clones were cleaved using about 20 of the most common restriction enzymes, which recognizes a sequence of 6 nucleotides and starting from cleavage pattern restriction maps were drafted. Two of the clones, pSDF100, and pSDF300, were partly overlapping having a 3.9 kb sequence in common, and thus only one was selected for further studies. A pSDF100 had a higher fibronectin binding activity than pSDF300 the former was selected.

pSDF100 and pSDF200 were subcloned in order to identify more closely the regions encoding fibronectin binding activity. pSDF100 was cleaved using Bam HI, whereupon the plasmid was religated. This clone with the Bam HI-Bam HI fragment deleted was called pSDF101 and was positive. pSDF101 was further cleaved using XbaI, which gave 3 fragments, one mainly consisting of the pUC18 vector. The other two XbaI—XbaI fragments were purified and inserted into the pUC18 vector. One of these fragments encodes fibronectin binding activity. This clone was called pSDF102. In the corresponding way subclones were constructed from pSDF200. The ClaI-SacI fragment deleted from pSDF200 gave a clone called pSDF201, and further the BglII-EcoRI fragment eliminated from pSDF201 gives pSDF202. Finally, the XhoI-EcoRI fragment has been deleted from pSDF202. This new clone was thereby obtained was called pSDF203. All these new subclones are positive, i.e., they express fibronectin binding activity, cf. FIG. 1*a* and FIG. 1*b*.

Further Subcloning by EcoIII Digestion

In order to facilitate the nucleotide sequencing according to the dideoxymethod smaller subclones differing 150 to 200 base pairs in length are required in order to obtain overlapping DNA sequence. Exonucleas III digest one of the DNA strands from the 5' overhang, or from the blunt end, but leaves the 3' overhang. The single stranded DNA is then digested using S1-nuclease. This technique is used in the "Erase-a-Base" System Kit (Promega, Madison, USA) and makes it possible to construct series of subclones which differs in some hundreds of nucleotides in size. In cases of interest the fibronectin binding activity was tested, cf. Table 1 below.

Table 1

Inhibition Assay in Tubes

Assay mixture: 100 µl of lysate of *E. coli* clones containing streptococcal DNA clones (the bacteria were grown on LB+50 µg ampicillin+1 mM IPTG, washed, and concentrated to $OD_{540}$=5.0) 100 µl Cowan I cells, heat killed, $OD_{540}$=5.0 100 µl $^{125}$I labelled fibronectin, 8865 cpm 200 µl PBS+0.1% BSA Incubation: 2 hrs, room temperature Washing: Twice in PBS+0.1% BSA+0.05% Tween The results are evident from Table 1 below.

| Lysate of subclone | Dilution of lysate | Number of cpm | % binding in relation to control without lysate |
|---|---|---|---|
| Control | Without lysate | 4430 | 100 |
| pSDF102c10 | undil | 550 | 12.4 |
|  | $10^{-2}$ | 3870 | 87.4 |
| pSDF102c13 | undil | 200 | 4.5 |
|  | $10^{-2}$ | 1440 | 32.5 |
| pSDF102c9 | undil | 610 | 13.8 |
|  | $10^{-2}$ | 3170 | 71.6 |
| pSDF102c11 | undil | 1400 | 31.6 |
|  | $10^{-2}$ | 3490 | 78.8 |
| pSDF102C14 | undil | 630 | 14.2 |
|  | $10^{-2}$ | 3220 | 72.7 |
| pSDF102c18 | undil | 4030 | 91.0 |
|  | $10^{-2}$ | 4300 | 97.1 |
| pSDF203c3 | undil | 640 | 14.4 |
|  | $10^{-2}$ | 2780 | 62.8 |
| pSDF203c6 | undil | 2710 | 61.2 |
|  | $10^{-2}$ | 4790 | 108 |
| pSDF203c8 | undil | 3180 | 71.8 |
|  | $10^{-2}$ | 3660 | 82.6 |
| pSDF203c11 | undil | 3540 | 79.9 |
|  | $10^{-2}$ | 3970 | 89.6 |
| pSDF203c15 | undil | 3860 | 87.1 |
|  | $10^{-2}$ | 4300 | 97.1 |
| pSDF203c9 | undil | 4020 | 90.7 |
|  | $10^{-2}$ | 4730 | 107 |
| PSDF102 | undil | 200 | 4.5 |
|  | $10^{-2}$ | 1050 | 23.7 |
| PSDF203 | undil | 180 | 4.1 |
|  | $10^{-2}$ | 950 | 21.4 |
| TG1 | undil | 3690 | 83.3 |

Nucleotide Sequencing

Subclones obtained after an exoIII digestion and other subclones were sequenced using the dideoxy method according to Gem Seq$^R$ dsDNA Sequ-encing System (Promega Biotech., Madison, USA)

Nucleotide sequencing of pSDF102 gave the following sequence (SEQ ID NO:1):

```
CTA GAT ACC TCA GAA AAC AAA AAA TCT GTA ACT GAA AAA GTA ATA ACT

AGC GAT GTT AAA TAT AAG ATT AAT GAT AAA GAA GTG AAA GGT AAA GAA

CTA GAC GAT GTC TCT TTA ACT TAC AGT AAA GAA ACC GTT CGT AAG CCA

CAG GTG GAA CCA AAT GTT CCT GAT ACA CCT CAG GAA AAA CCA TTG ACA

CCG CTT GCA CCG TCA GAA CCT TCA CAA CCA TCT ATT CCA GAG ACA CCA

CTG ATA CCG TCA GAA CCT TCA GTT CCA GAG ACA TCA ACA CCA GAA GGT

CCA ACA GAG GGA GAA AAT AAT CTT GGT GGT CAG AGT GAA ATA ACG ATT

ACA GAA GAT TCT CAA TCA GGG ATG TCT GGT CAA AAT CCT GGT TCT GGA

AAT GAA ACA GTG GTT

GAA GAC ACT CAA ACA AGT CAA GAG GAT ATT GTA CTT GGT GGT CCA GGT

CAA GTG ATT GAC TTT ACA GAA GAT AGC CAA CCG GGT ATG TCT GGT AAT

AAT AGC CAT ACT ATT ACA

GAA GAT TCT AAA CCA AGT CAA GAG GAT GAG GTG ATA ATC GGC GGT CAA

GGT CAG GTG ATT GAC TTT ACA GAA GAT ACT CAA TCT GGT ATG TCT GGG

GAT AAT AGC CAT ACA GAT GGG ACA GTG CTT GAA

GAA GAC TCT AAA CCA AGT CAA GAG GAT GAG GTG ATA ATC GGC GGT CAA

GGT CAA GTG ATT GAC TTT ACA GAA GAT ACC CAA ACC GGT ATG TCT GGG

GCT GGA CAA GTA GAG AGT CCA ACA ACT ACC GAA GAA ACC CAT AAA CCA

GAA ATA ATC ATG GGC GGT CAA AGT GAC CCT ATT GAT ATG GTT GAG GAC
```

```
ACT CTT CCT GGT ATG TCT GGC TCT AAT GAA GCT ACT GTT GTG GAA GAA

GAC ACA CGT CCT AAA CTT CAA TTC CAT TTT GAT AAT GAA GAG CCC GTT

CCT GCA ACG TTT CCA ACC GTT TCT CAA ACT CCT ATT GCT CAG GTA GAA

AGT AAA GTG CCT CAT GCC AAA GCA GAG AGT GCG TTA CCT CAA ACT GGA

GAT ACA AAT AAA CTA GAA ACG TTC TTT ACC ATT ACA GCA CTA ACT GTT

ATT GGA GCG GCA GGA TTA CTA GGC AAA AAA CGT CGT AAT AAT CAA ACT

GAT TAA TCA GCA GAT TTC ATC AAA CGC TAT AAA CAA GGC TAA CAT TTT

AGC CTT GTT TTA TAT TGT TTC ACT GAC CTC TAA AAG TTA TGA CTG TTT

TAA AGG GGG GGT AGG CCA ATC CTC AAA AGT AGT TAA GTT GAG AAA CAC

CAC ATC ACT TTA GTC TTA CTG CGC ATA CTA AAA GCA AAA GAT AAT TAG

GAG CAG TTG CTA ACT GGA AAA AAT CAA ATG CAA AGC TAG TTG CCA AAG

AAC TCT AGA
``` whereby the repetitive domains of the sequence (SEQ ID NO: 3)

The nucleotide sequencing of pSDF203 gave the following sequence (SEQ ID NO: 2)

```
GAA GAC ACT CAA ACA AGT CAA GAG GAT ATT GTA CTT GGT GGT CCA GGT

CAA GTG ATT GAC TTT ACA GAA GAT AGC CAA CCG GGT ATG TCT GGT AAT

AAT AGC CAT ACT ATT ACA

GAA GAT TCT AAA CCA AGT CAA GAG GAT GAG GTG ATA ATC GGC GGT CAA

GGT CAG GTG ATT GAC TTT ACA GAA GAT ACT CAA TCT GGT ATG TCT GGG

GAT AAT AGC CAT ACA GAT GGG ACA GTG CTT GAA

GAA GAC TCT AAA CCA AGT CAA GAG GAT GAG GTG ATA ATC GGC GGT CAA

GGT CAA GTG ATT GAC TTT ACA GAA GAT ACC CAA ACC GGT ATG TCT GGG
``` encode a peptide having fibronectin binding activity.

```
CTC GAG GAA ACT TTG CCA AAC GAG GAA CAT CAA TCA GGT GAT ACC ACA

ACT ATT GAA GAT ACT CGC CCG ATT GAT ACC ATG TCA GGT CTA TCA GGA

GAG ACT GGG CAG TCT GGT AAT ACT ACA ATT GAG GAA GAT AGT ACG ACT

CAC GTT AAA TTC TCA AAA CGT GAT ATT AAT GGT AAA GAA CTA GCA GGT

GCT ATG ATT GAA CTA CGT AAT CTA TCA GGT CAA ACT ATT CAA TCA TGG

ATA TCA GAC GGC ACA GTT AAA GTT TTC TAC TTG ATG CCA GGG ACT TAT

CAA TTT GTG GAG ACG GCA GCG CCA GAA GGT TAT GAA TTG CAA GCT CCA

ATT ACC TTC ACA ATT GAT GAG AAA GGA CAA ATT TGG GTA GAC AGT ACA

ATT ACT GAG GCG AGT CAA TCT ATT GAT TTC

GAG GAA ACT TTA CCA ACT GAA CAA GGC CAA TCT GGC TCT ACA ACG GAG

GTT GAG GAT ACT AAA GGC CCA GAA GTC ATT ATC GGC GGT CAG GGA GAG

ATT GTT GAT ATC

GAG GAG AAC TTA CCA ACT GAA CAA GGC CAA TCT GGC TCT ACA ACT GAA

GTA GAG GAT ACT AAA GGC CCA GAA GTC ATT ATC GGC GGT CAA GGA GAG
```

```
GTT GTT GAT ATT

GAG GAG AGC TTA CCA ACT GAA CAA GGC CAA TCT GGC TCT ACA ACT GAA

GTA GAA GAT

AGC AAG CCT AAA CTC TCT ATC CAC TTT GAT AAC GAG TGG CCT AAG GAA

GAC AAA CCA CAA CTA CCT GCC GTT GAA AAA CCT AAG ACT AAG GAG AGC

TTG CCA GCC GCA GGG GAA GCT GAA CAT GTC TTA TCT ACT ATC GTG GGA

GCA ATG ATC
``` whereby the repetitive domains of the sequence (SEQ ID NO: 4)

```
GAG GAA ACT TTA CCA ACT GAA CAA GGC CAA TCT GGC TCT ACA ACG GAG

GTT GAG GAT ACT AAA GGC CCA GAA GTC ATT ATC GGC GGT CAG GGA GAG

ATT GTT GAT ATC

GAG GAG AAC TTA CCA ACT GAA CAA GGC CAA TCT GGC TCT ACA ACT GAA

GTA GAG GAT ACT AAA GGC CCA GAA GTC ATT ATC GGC GGT CAA GGA GAG

GTT GTT GAT ATT

GAG GAG AGC TTA CCA ACT GAA CAA GGC CAA TCT GGC TCT ACA ACT GAA

GTA GAA GAT
``` encode a peptide having fibronectin binding activity.

Souther blot hybridisation detects no homologies on DNA level between the genes for the fibronectin binding protein of S. aureus, and the corresponding genes from S. dysgalactiae. The competitive inhibition between the proteins from the respective species depends most probably on the fact that their binding sites in the fibronectin within the NH$_2$ terminal 29 kD fragment are close to each other and thereby sterically block the binding.

Western blot analyses of lysate of the two fibronectin binding E. coli clones studied indicate using $^{125}$I labelled fibronectin and autoradiography shows that subclone pSDF203 encodes a protein having a molecular weight of 70 kDa, and subclone pSDF102 a corresponding protein having a molecular weight of 110 kD.

The deduced amino acid sequences [SEQ ID NOS.: 5 & 6] of the protein or polypeptides from the above given nucleotide sequences encode for are the following:

```
Glu Asp Thr Gln Thr Ser Gln Glu Asp Ile Val Leu Gly Gly Pro Gly

Gln Val Ile Asp Phe Thr Glu Asp Ser Gln Pro Gly Met Ser Gly Asn

Ser His Thr Ile Thr

Glu Asp Ser Lys Pro Ser Gln Glu Asp Glu Val Ile Ile Gly Gly Gln

Gly Gln Val Ile Asp Phe Thr Glu Asp Thr Gln Ser Gly Met Ser Gly

Asp Asn Ser His Thr Asp Gly Thr Val Leu Glu

Glu Asp Ser Lys Pro Ser Gln Glu Asp Glu Val Ile Ile Gly Gly Gln

Gly Gln Val Ile Asp Phe Thr Glu Asp Thr Gln Thr Gly Met Ser Gly and

Glu Glu Thr Leu Pro Thr Glu Gln Gly Gln Ser Gly Ser Thr Thr Glu

Val Glu Asp Thr Lys Gly Pro Glu Val Ile Ile Gly Gly Gln Gly Glu

Ile Val Asp Ile

Glu Glu Asn Leu Pro Thr Glu Gln Gly Gln Ser Gly Ser Thr Thr Glu
```

```
-continued
Val Glu Asp Thr Lys Gly Pro Glu Val Ile Ile Gly Gly Gln Gly Glu

Val Val Asp Ile

Glu Glu Ser Leu Pro Thr Glu Gln Gly Gln Ser Gly Gly Ser Thr Thr

Glu Val Glu Asp,
``` respectively.

The present fibronectin binding proteins can be used in immunization, whereby the proteins, preferably in combination with a fusion protein in order to form a larger antigen to react upon, are injected in doses creating an immunological reaction in the host mammal. Thus the fibronectin binding proteins can be used in vaccination of rumens to mastitis created by streptococcal infections.

Further, the fibronectin binding proteins can be used to block an infection in an open skin lesion. Wounds can be treated by using a suspension comprising the fibronectin binding protein. Thus the fibronectin binding proteins can be used to treat wounds, e.g., for blocking bacterial binding sites in fibronectin, or for immunization (vaccination). In the latter case the host produces specific antibodies which can protect against attachment by bacterial strains comprising such fibronectin binding proteins. Hereby the antibodies block the adherence of the bacterial strains to damaged tissue.

Examples of colonizing of the tissue damage are:
a) colonizing of wounds in skin and connective tissue, which wounds have been caused by a mechanical trauma, chemical damage, and/or thermical damage;
b) colonizing of wounds on mucous membranes such as in the mouth cavity, or in the mammary glands, urethra or vagina;
c) colonizing of connective tissue proteins, which have been exposed by minimal tissue damage (micro lesions) in connection with epithelium and endothelium (mastitis, heart valve infection, hip exchange surgery).

When using the present fibronectin binding proteins, prepared by means of hybrid-DNA technique, or synthesized, for immunization (vaccination) in mammals, including humans, the proteins, or polypeptides are dispersed in sterile isotonic saline solution, optionally while adding a pharmaceutically acceptable dispersing agent. Different types of adjuvants can further be used in order to sustain the release in the tissue, and thus expose the protein for a longer period of time to the immuno defence system of a body.

A suitable dose to obtain immunization is 0.5 to 5 μg of fibronectin binding protein per kg body weight and injection at immunization. In order to obtain durable immunization, vaccinations should be carried out at consecutive occasions with an interval of 1 to 3 weeks, preferably at three occasions. Adjuvants are normally not added when repeating the immunization treatment.

When using the present fibronectin binding proteins or polypeptides for local topical administration the protein is dispersed in an isotonic saline solution to a concentration of 25 to 250 μg per ml. The wounds are then treated with such an amount only to obtain a complete wetting of the wound surface. For an average wound thus only a couple of milliliters of solution are used in this way. After treatment using the protein solution the wounds are suitably washed with isotonic saline solution or another suitable wound treatment solution.

Further the fibronectin binding protein, or synthesized polypeptide of the present invention can be used to diagnoze bacterial infections caused by *S. dysgalactiae* strains, whereby a fibronectin binding protein of the present invention is immobilized on a solid carrier, such as small latex or Sepharose$^R$ beads, whereupon sera containing antibodies are allowed to pass and react with the fibronectin binding protein thus immobilized. The agglutination is then measured by known methods.

Further the fibronectin binding protein or polypeptide can be used in an ELISA test (Enzyme Linked Immuno Sorbent Assay; E Engvall, Med. Biol. 55, 193 (1977)). Hereby wells in a polystyrene microtitre plate are coated with the fibronectin binding protein and incubated over night at 4° C. The plates are then thoroughly washed using PBS containing 0.05% Tween 20, and dried. Serial dilutions of the patient serum made in PBS-Tween, are added to the wells, and are incubated at 30° C. for 1.5 hrs. After rinsing anti-human IgG conjugated with an enzyme, or a horseradish peroxidase, or an alkaline phosphatase is added to the wells and further incubated at 30° C. for 1.5 hrs. During these incubations IgG from patient serum, and added antihuman IgG-enzyme conjugate, respectively, has been bound thereto. After rinsing, an enzyme substrate is added, p-nitrophosphate in case of an alkaline phosphatase, or orthophenylene diamine substrate (OPD) in case a peroxidase has been used, respectively. The wells of the plates are then rinsed using a citrate buffer containing 0.055% OPD, and 0.005% $H_2O_2$, and incubated at 30° C. for 10 min. The enzyme reaction is stopped by adding a 4N solution of $H_2SO_4$ to each well. The colour development is measured using a spectrophotometer.

Depending on the type of enzyme substrate used a fluoroscence measurement can be used as well.

Another method to diagnoze *S. dysgalactiae* infections is by using the DNA gene probe method based on the nucleotide sequence for the fibronectin binding protein or part thereof. Thereby the natural or synthetic DNA sequence is attached to a solid carrier, such as a nitrocellulose filter, a nylon filter, or a polystyrene plate as mentioned above, by e.g., adding a milk in the case of diagnozing a mastitis, to the surface. The DNA gene probe, optionally labelled enzymatically, or by a radioactive isotope, is then added to the solid surface plate comprising the DNA sequence, whereby the DNA gene probe attaches to the membrane associated sequence where appearing. The enzyme or radioactive isotope can readily be determined by known methods.

Above the term fibronectin binding protein includes any of the polypeptide sequences as well, which constitute the minimal fibronectin binding site of the complete protein.

Legends to the Figures

FIG. 1 Restriction Map

FIG. 1a. Restriction map and subclones of the 5 kb insert from *S. dysgalactiae* in the pUC18-vector called pSDF100.

FIG. 1b. Restriction map and subclones of the 6.9 kb insert from *S. dysgalactiae* in the pUC18-vector called pSDF200.

A. Restriction map of the clone.

B. Different subclones constructed to determine the region in the gene which codes for fibronectin binding activity. The binding activity of the different gene products have been indicated.

C. Subclones obtained after digestion with ExoIII of pSDF102, and pSDF203, respectively. Scale: 1 cm=100 bp. M is the part of the DNA sequence which encodes the membrane associated part of the protein (=COOH-terminal). Subclone p102c10 contains the 3' end of the gene (FIG. 1a). $A_1$, $A_2$ och $A_3$, and $B_1$, $B_2$, and $B_3$, respectively, denote repetitive domains of the sequences (cf. FIG. 3 [SEQ ID NOS.: 7 & 8])

FIG. 2 Inhibition Assay in Tubes

Binding of $^{125}I$ labelled fibronectin to cells of *S. dysgalactiae* S2, and *S. aureus* Cowan I, respectively, at the addition of lysates of *E. coli*-clones. The percentage values given are related to the binding of $^{125}I$ labelled fibronectin to cells in the absence of lysate. As a negative control a lysate of *E. coli* TG1 with pUC18-vector without insert was used, which had no influence on the binding of the cells to fibronectin. *E. coli* clone 015 contains a gene from *S. aureus* encoding for fibronectin binding activity.

FIG. 3 [SEQ ID NOS.: 7 & 8] shows repetitive sequences of pSDF102 och pSDF203.

FIG. 4 (SEQ ID NO: 9) shows the nucleotide and deducted amino acid sequences of pSDF102.

FIG. 5 (SEQ ID NO: 10) shows the nucleotide and deducted amino acid sequences of pSDF203

REFERENCES

Figure 1A:
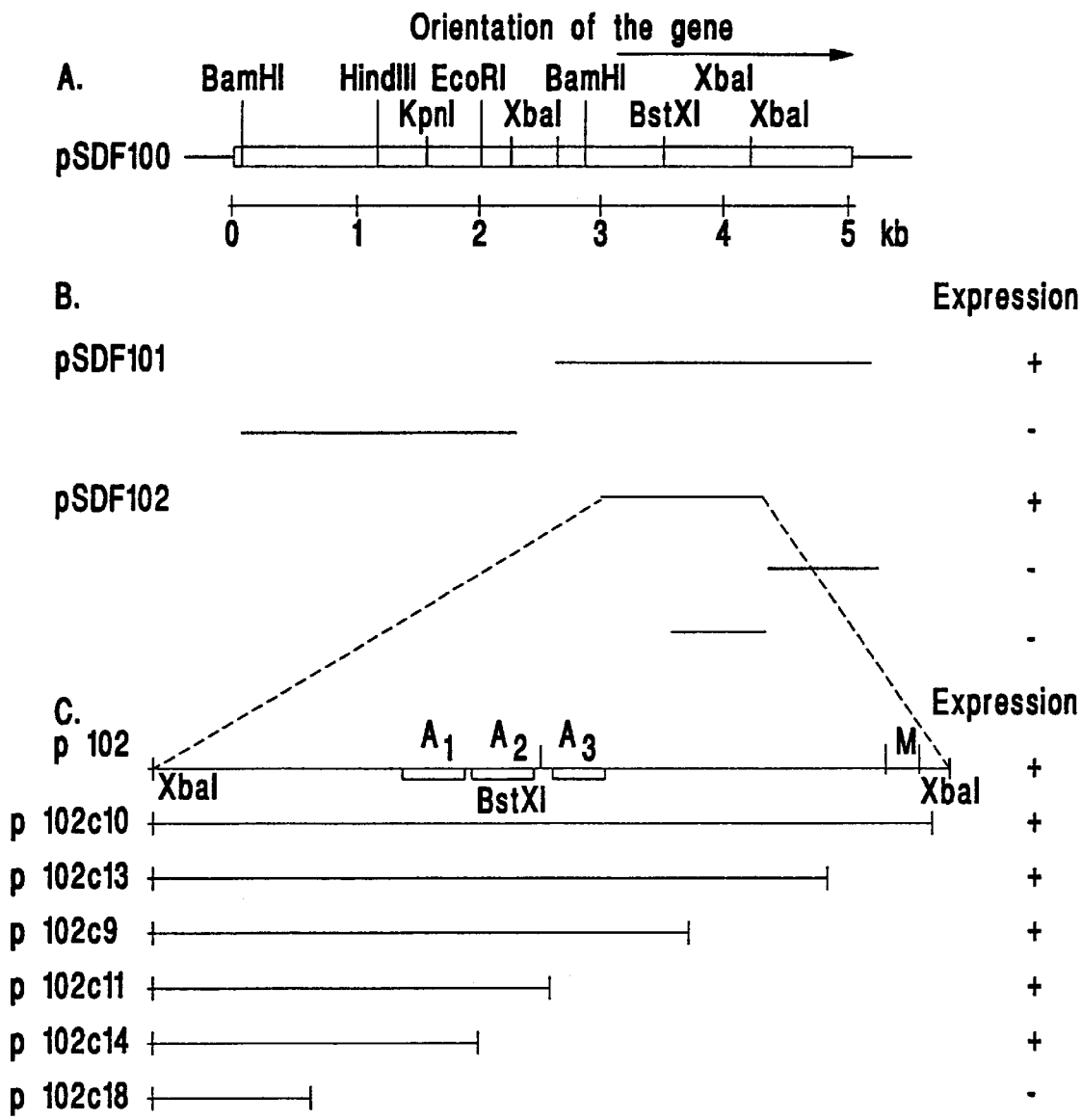
Figure 1B:
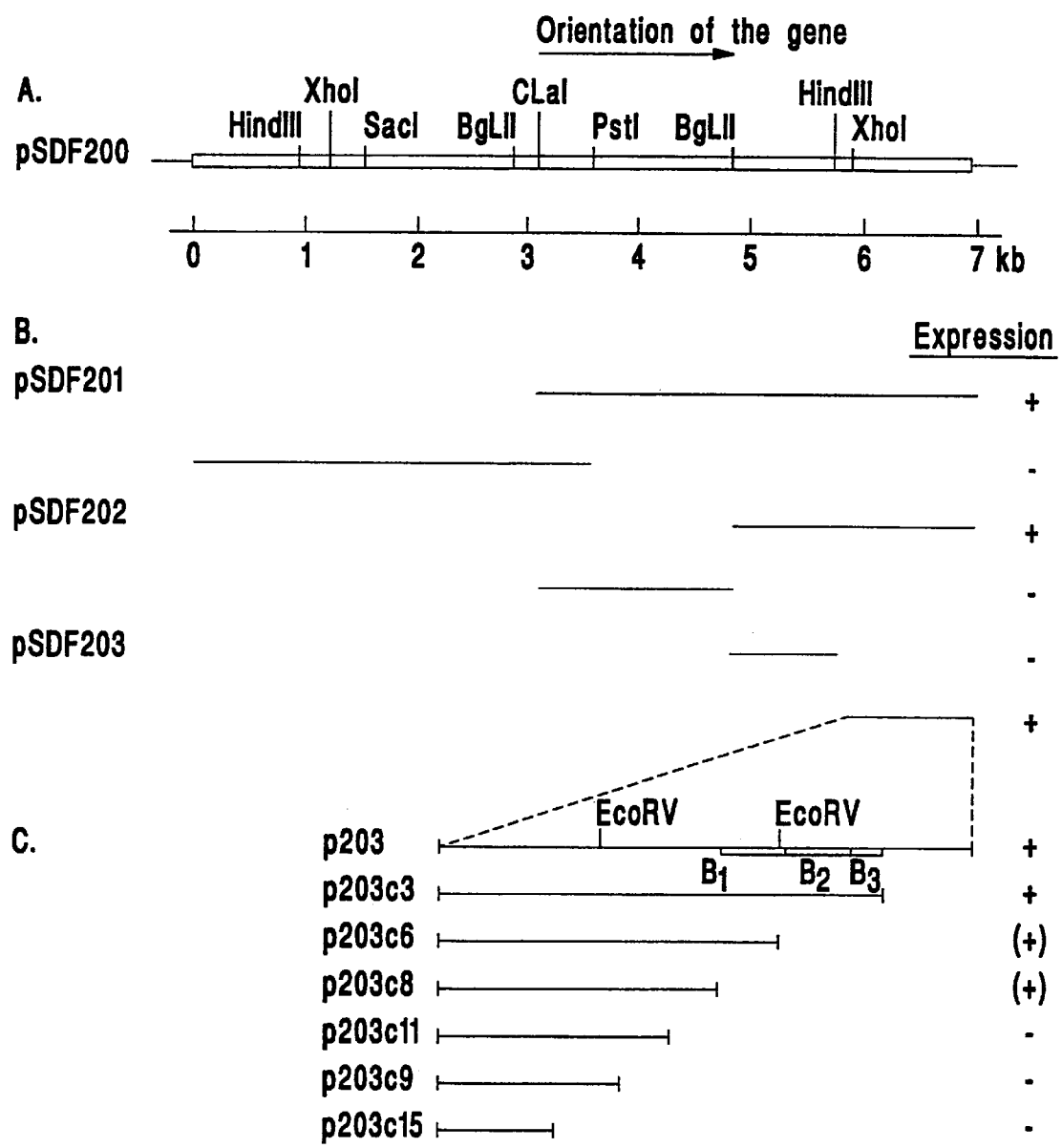
Figure 2:
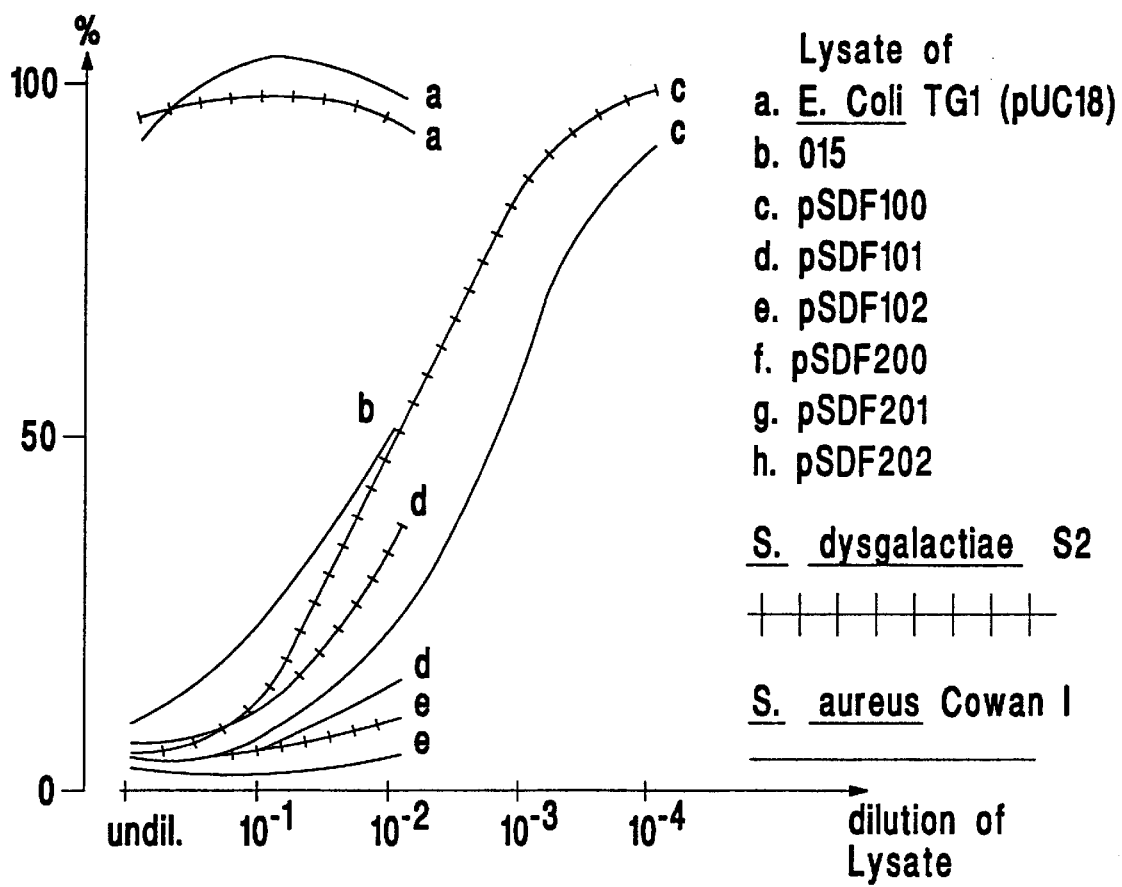
Figure 2:
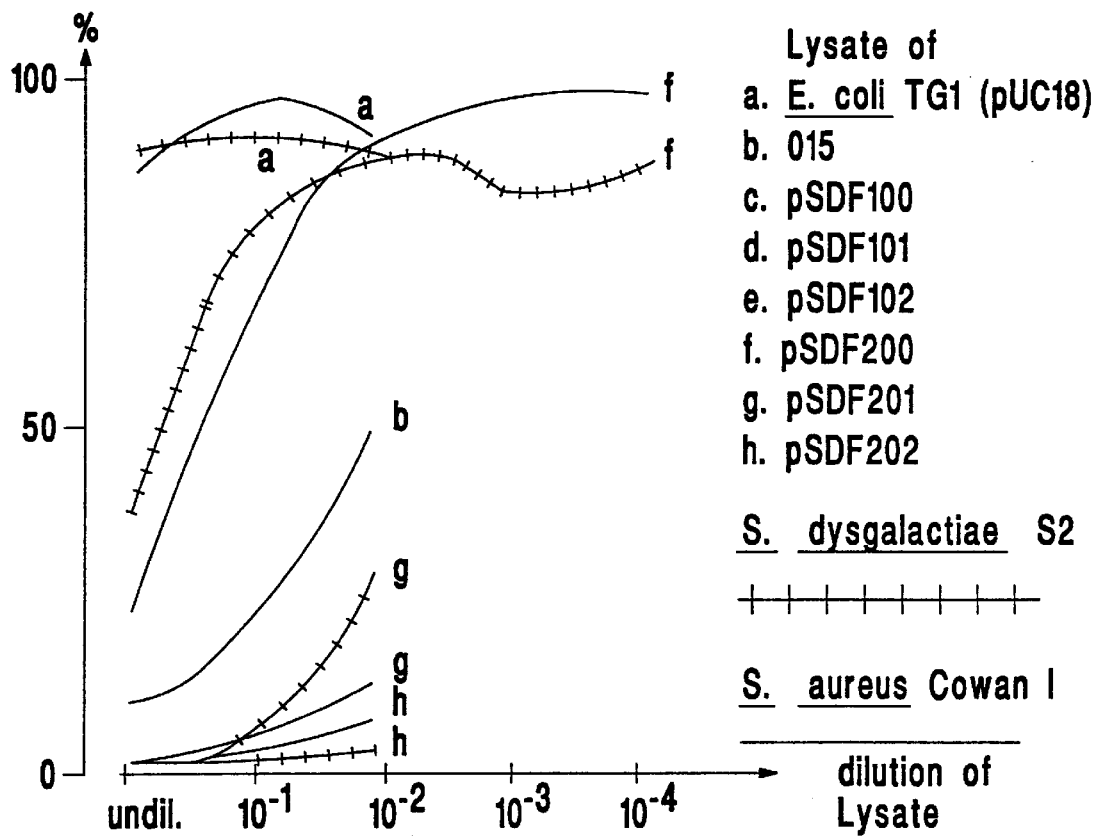

1. Hymes, R. O. (1985) Annu. Rev. Cell Biol. 1, 67–90.
2. Kuusela, P. (1978) Nature 276, 718–720.
3. Switalski, L. et al (1982) Eur. J. Clin. Microbiol. 1, 381–387.
4. Fröman, G. et al. (1984) J. Biol. Chem. 259, 14899–14905.
5. Baloda, S. B. et al (1985) FEMS Microbiol. Lett. 28, 1–5.
6. Wadström, T. et al (1985) In Jackson, G. J. (ed), Pathogenesis of Infection, Springer Verlag, Berlin, Heidelberg, New York, Tokyo, pp. 193–207.
7. Lopes, J. D. et al (1985) Science 229, 275–277.
8. Langone, I. I. (1982) Adv. Immunol. 32, 157–252.
9. Marmur, J. (1961) J. Mol. Biol. 3, 208–218.
10. Flock, J.-I. et al (1987) The EMBO Journal 6, 2351–2357.
11. Monstein, H.-J. et al (1986) Biochem. Int. 12, 889–896.

We claim:

1. A pharmaceutical composition for the treatment of infections caused by S. dysgalactiae which comprises at least one protein or polypeptide derived from S. dysgalactiae having fibronectin binding properties together with a pharmaceutically acceptable carrier or diluent.

2. A method for the treatment of infections caused by S. dysgalactiae in mammals, comprising administering to said mammal a therapeutically active amount of at least one fibronectin binding protein or polypeptide derived from S. dysgalactiae, together with a pharmaceutically acceptable carrier or diluent.

3. A method for preventing or treating mastitis in a ruminant, comprising vaccinating a ruminant with a protein derived from S. dysgalactiae in an amount which is effective to elicit production of antibodies against said S. dysgalactiae bacterial strain, wherein said protein comprises an amino acid sequence selected from the group consisting of:

```
Glu Asp Thr Gln Thr Ser Gln Glu Asp Ile Val Leu Gly Gly Pro Gly     (SEQ ID NO: 5)
Gln Val Ile Asp Phe Thr Glu Asp Ser Gln Pro Gly Met Ser Gly Asn
Ser His Thr Ile Thr
Glu Asp Ser Lys Pro Ser Gln Glu Asp Glu Val Ile Ile Gly Gly Gln
Gly Gln Val Ile Asp Phe Thr Glu Asp Thr Gln Ser Gly Met Ser Gly
Asp Asn Ser His Thr Asp Gly Thr Val Leu Glu
Glu Asp Ser Lys Pro Ser Gln Glu Asp Glu Val Ile Ile Gly Gly Gln
Gly Gln Val Ile Asp Phe Thr Glu Asp Thr Gln Thr Gly Met Ser Gly;
and
Glu Glu Thr Leu Pro Thr Glu Gln Gly Gln Ser Gly Ser Thr Thr Glu     (SEQ ID NO: 6)
Val Glu Asp Thr Lys Gly Pro Glu Val Ile Ile Gly Gly Gln Gly Glu
Ile Val Asp Ile
Glu Glu Asn Leu Pro Thr Glu Gln Gly Gln Ser Gly Ser Thr Thr Glu
Val Glu Asp Thr Lys Gly Pro Glu Val Ile Ile Gly Gly Gln Gly Glu
Val Val Asp Ile
Glu Glu Ser Leu Pro Thr Glu Gln Gly Gln Ser Gly Gly Ser Thr Thr
Glu Val Glu Asp.
```

4. A method for preventing or treating mastitis in a ruminant, comprising vaccinating a ruminant with a protein derived from *S. dysgalactiae* in an amount which is effective to elicit production of antibodies against said *S. dysgalactiae* bacterial strain, wherein said protein is encoded by a DNA sequence selected from the group consisting of:

```
CTA GAT ACC TCA GAA AAC AAA AAA TCT GTA ACT GAA AAA GTA ATA ACT     (SEQ ID NO: 9)
AGC GAT GTT AAA TAT AAG ATT AAT GAT AAA GAA GTG AAA GGT AAA GAA
CTA GAC GAT GTC TCT TTA ACT TAC AGT AAA GAA ACC GTT CGT AAG CCA
CAG GTG GAA CCA AAT GTT CCT GAT ACA CCT CAG GAA AAA CCA TTG ACA
CCG CTT GCA CCG TCA GAA CCT TCA CAA CCA TCT ATT CCA GAG ACA CCA
CTG ATA CCG TCA GAA CCT TCA GTT CCA GAG ACA TCA ACA CCA GAA GGT
CCA ACA GAG GGA GAA AAT AAT CTT GGT GGT CAG AGT GAA GAG ATA ACG
ATT ACA GAA GAT TCT CAA TCA GGG ATG TCT GGT CAA AAT CCT GGT TCT
GGA AAT GAA ACA GTG GTT
GAA GAC ACT CAA ACA AGT CAA GAG GAT ATT GTA CTT GGT GGT CCA GGT
CAA GTG ATT GAC TTT ACA GAA GAT AGC CAA CCG GGT ATG TCT GGT AAT
AAT AGC CAT ACT ATT ACA
GAA GAT TCT AAA CCA AGT CAA GAG GAT GAG GTG ATA ATC GGC GGT CAA
GGT CAG GTG ATT GAC TTT ACA GAA GAT ACT CAA TCT GGT ATG TCT GGG
GAT AAT AGC CAT ACA GAT GGG ACA GTG CTT GAA
GAA GAC TCT AAA CCA AGT CAA GAG GAT GAG GTG ATA ATC GGC GGT CAA
GGT CAA CTG ATT GAC TTT ACA GAA GAT ACC CAA ACC GGT ATG TCT GGG
GCT GGA CAA GTA GAG AGT CCA ACA ACT ACC GAA GAA ACC CAT AAA CCA
GAA ATA ATC ATG GGC GGT CAA AGT GAC CCT ATT GAT ATG GTT GAG GAC
```

-continued

ACT CTT CCT GGT ATG TCT GGC TCT AAT GAA GCT ACT GTT GTG AAA GAA
GAC ACA CGT CCT AAA CTT CAA TTC CAT TTT GAT AAT GAA GAG CCC GTT
CCT GCA ACG GTT CCA ACC GTT TCT CAA ACT CCT ATT GCT CAG GTA GAA
AGT AAA GTG CCT CAT GCC AAA GCA GAG AGT GCG TTA CCT CAA ACT GGA
GAT ACA AAT AAA CTA GAA ACG TTC TTT ACC ATT ACA GCA CTA ACT GTT
ATT GGA GCG GCA GGA TTA CTA GGC AAA AAA CGT CGT AAT AAT CAA ACT
GAT TTA TCA GCA GAT TTC ATC AAA CGC TAT AAA CAA GGC TAA CAT TTT
AGC CTT GTT TTA TAT TGT TTC ACT GAC CTC TAA AAG TTA TGA CTG TTT
TAA AGG GGG GGT AGG CCA ATC CTC AAA AGT AGT TAA GTT GAG AAA CAC
CAC ATC ACT TTA GTC TTA CTG CGC ATA CTA AAA GCA AAA GAT AAT TAG
GAG CAG TTG CTA ACT GGA AAA AAT CAA ATG CAA AGC TAG TTG CCA AAG
AAC TCT AGA;

GAA GAC ACT CAA ACA AGT CAA GAG GAT ATT GTA CTT GGT GGT CCA GGT    (SEQ ID NO: 3)
CAA GTG ATT GAC TTT ACA GAA GAT AGC CAA CCG GGT ATG TCT GGT AAT
AAT AGC CAT ACT ATT ACA
GAA GAT TCT AAA CCA AGT CAA GAG GAT GAG GTG ATA ATC GGC GGT CAA
GGT CAG GTG ATT GAC TTT ACA GAA GAT ACT CAA TCT GGT ATG TCT GGG
GAT AAT AGC CAT ACA GAT GGG ACA GTG CTT GAA
GAA GAC TCT AAA CCA AGT CAA GAG GAT GAG GTG ATA ATC GGC GGT CAA
GGT CAA CTG ATT GAC TTT ACA GAA GAT ACC CAA ACC GGT ATG TCT GGG;

CTC GAG GAA ACT TTG CCA AAC GAG GAA CAT CAA TCA GGT GAT ACC ACA    (SEQ ID NO: 2)
ACT ATT GAA GAT ACT CGC CCG ATT GAT ACC ATG TCA GGT CTA TCA GGA
GAG ACT GGG CAG TCT GGT AAT ACT ACA ATT GAG GAA GAT AGT ACG ACT
CAC GTT AAA TTC TCA AAA CGT GAT ATT AAT GGT AAA GAA CTA GCA GGT
GCT ATG ATT GAA CTA CGT AAT CTA TCA GGT CAA ACT ATT CAA TCA TGG
ATA TCA GAC GGC ACA GTT AAA GTT TTC TAC TTG ATG CCA GGG ACT TAT
CAA TTT GTG GAG ACG GCA GCG CCA GAA GGT TAT GAA TTG CAG CTT CCA
ATT ACC TTC ACA ATT GAT GAG AAA GGA CAA ATT TGG GTA GAC AGT ACA
ATT ACT GAG GCG AGT CAA TCT ATT GAT TTC
GAG GAA ACT TTA CCA ACT GAA CAA GGC CAA TCT GGC TCT ACA ACG GAG
GTT GAG GAT ACT AAA GGC CCA GAA GTC ATT ATC GGC GGT CAG GGA GAG
ATT GTT GAT ATC
GAG GAG AAC TTA CCA ACT GAA CAA GGC CAA TCT GGC TCT ACA ACT GAA
GTA GAG GAT ACT AAA GGC CCA GAA GTC ATT ATC GGC GGT CAA GGA GAG
GTT GTT GAT ATT
GAG GAG AGC TTA CCA ACT GAA CAA GGC CAA TCT GGC TCT ACA ACT GAA
GTA GAA GAT
AGC AAG CCT AAA CTC TCT ATC CAC TTT GAT AAC GAG TGG CCT AAG GAA
GAC AAA CCA CAA CTA CCT GCC GTT GAA AAA CCT AAG ACT AAG GAG AGC
TTG CCA GCC GCA GGG GAA GCT GAA CAT GTC TTA TCT ACT ATC GTG GGA

-continued

```
GCA ATG ATC;

and

GAG GAA ACT TTA CCA ACT GAA CAA GGC CAA TCT GGC TCT ACA ACG GAG       (SEQ ID NO: 4)

GTT GAG GAT ACT AAA GGC CCA GAA GTC ATT ATC GGC GGT CAG GGA GAG

ATT GTT GAT ATC

GAG GAG AAC TTA CCA ACT GAA CAA GGC CAA TCT GGC TCT ACA ACT GAA

GTA GAG GAT ACT AAA GGC CCA GAA GTC ATT ATC GGC GGT CAA GGA GAG

GTT GTT GAT ATT

GAG GAG AGC TTA CCA ACT GAA CAA GGC CAA TCT GGC TCT ACA ACT GAA

GTA GAA GAT.
```

5. A composition of matter comprising at least one protein or polypeptide isolated from S. *dysgalactiae* and a carrier therefor, wherein said protein or polypeptide has fibronectin binding properties.

6. A method for the treatment of infections caused by S. *dysgalactiae* in mammals, comprising administering to said mammal a therapeutically active amount of at least one fibronectin binding protein or polypeptide derived from S. *dysgalactiae*.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1371 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CTAGATACCT CAGAAAACAA AAAATCTGTA ACTGAAAAAG TAATAACTAG CGATGTTAAA         60

TATAAGATTA ATGATAAAGA AGTGAAAGGT AAAGAACTAG ACGATGTCTC TTTAACTTAC        120

AGTAAAGAAA CCGTTCGTAA GCCACAGGTG GAACCAAATG TTCCTGATAC ACCTCAGGAA        180

AAACCATTGA CACCGCTTGC ACCGTCAGAA CCTTCACAAC CATCTATTCC AGAGACACCA        240

CTGATACCGT CAGAACCTTC AGTTCCAGAG ACATCAACAC CAGAAGGTCC AACAGAGGGA        300

GAAAATAATC TTGGTGGTCA GAGTGAAATA ACGATTACAG AAGATTCTCA ATCAGGGATG        360

TCTGGTCAAA ATCCTGGTTC TGGAAATGAA ACAGTGGTTG AAGACACTCA AACAAGTCAA        420

GAGGATATTG TACTTGGTGG TCCAGGTCAA GTGATTGACT TTACAGAAGA TAGCCAACCG        480

GGTATGTCTG GTAATAATAG CCATACTATT ACAGAAGATT CTAAACCAAG TCAAGAGGAT        540

GAGGTGATAA TCGGCGGTCA AGGTCAGGTG ATTGACTTTA CAGAAGATAC TCAATCTGGT        600

ATGTCTGGGG ATAATAGCCA TACAGATGGG ACAGTGCTTG AAGAAGACTC TAAACCAAGT        660

CAAGAGGATG AGGTGATAAT CGGCGGTCAA GGTCAACTGA TTGACTTTAC AGAAGATACC        720

CAAACCGGTA TGTCTGGGGC TGGACAAGTA GAGAGTCCAA CAACTACCGA AGAAACCCAT        780

AAACCAGAAA TAATCATGGG CGGTCAAAGT GACCCTATTG ATATGGTTGA GGACACTCTT        840

CCTGGTATGT CTGGCTCTAA TGAAGCTACT GTTGTGGAAG AAGACACACG TCCTAAACTT        900

CAATTCCATT TTGATAATGA AGAGCCCGTT CCTGCAACGG TTCCAACCGT TTCTCAAACT        960

CCTATTGCTC AGGTAGAAAG TAAAGTGCCT CATGCCAAAG CAGAGAGTGC GTTACCTCAA       1020
```

```
                                   -continued

ACTGGAGATA CAAATAAACT AGAAACGTTC TTTACCATTA CAGCACTAAC TGTTATTGGA    1080

GCGGCAGGAT TACTAGGCAA AAAACGTCGT AATAATCAAA CTGATTTATC AGCAGATTTC    1140

ATCAAACGCT ATAAACAAGG CTAACATTTT AGCCTTGTTT TATATTGTTT CACTGACCTC    1200

TAAAAGTTAT GACTGTTTTA AAGGGGGGGT AGGCCAATCC TCAAAAGTAG TTAAGTTGAG    1260

AAACACCACA TCACTTTAGT CTTACTGCGC ATACTAAAAG CAAAGATAAA TTAGGAGCAG    1320

TTGCTAACTG GAAAAAATCA AATGCAAAGC TAGTTGCCAA AGAACTCTAG A             1371

(2) INFORMATION FOR SEQ ID NO:2:

(i) SEQUENCE CHARACTERISTICS:
          (A) LENGTH: 840 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:2:

CTCGAGGAAA CTTTGCCAAA CGAGGAACAT CAATCAGGTG ATACCACAAC TATTGAAGAT      60

ACTCGCCCGA TTGATACCAT GTCAGGTCTA TCAGGAGAGA CTGGGCAGTC TGGTAATACT     120

ACAATTGAGG AAGATAGTAC GACTCACGTT AAATTCTCAA AACGTGATAT TAATGGTAAA     180

GAACTAGCAG GTGCTATGAT TGAACTACGT AATCTATCAG GTCAAACTAT TCAATCATGG     240

ATATCAGACG GCACAGTTAA AGTTTTCTAC TTGATGCCAG GGACTTATCA ATTTGTGGAG     300

ACGGCAGCGC CAGAAGGTTA TGAATTGGCA GCTCCAATTA CCTTCACAAT TGATGAGAAA     360

GGACAAATTT GGGTAGACAG TACAATTACT GAGGCGAGTC AATCTATTGA TTTCGAGGAA     420

ACTTTACCAA CTGAACAAGG CCAATCTGGC TCTACAACGG AGGTTGAGGA TACTAAAGGC     480

CCAGAAGTCA TTATCGGCGG TCAGGGAGAG ATTGTTGATA TCGAGGAGAA CTTACCAACT     540

GAACAAGGCC AATCTGGCTC TACAACTGAA GTAGAGGATA CTAAAGGCCC AGAAGTCATT     600

ATCGGCGGTC AAGGAGAGGT TGTTGATATT GAGGAGAGCT TACCAACTGA ACAAGGCCAA     660

TCTGGCTCTA CAACTGAAGT AGAAGATAGC AAGCCTAAAC TCTCTATCCA CTTTGATAAC     720

GAGTGGCCTA AGGAAGACAA ACCACAACTA CCTGCCGTTG AAAAACCTAA GACTAAGGAG     780

AGCTTGCCAG CCGCAGGGGA AGCTGAACAT GTCTTATCTA CTATCGTGGG AGCAATGATC     840

(2) INFORMATION FOR SEQ ID NO:3:

(i) SEQUENCE CHARACTERISTICS:
          (A) LENGTH: 339 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:3:

GAAGACACTC AAACAAGTCA AGAGGATATT GTACTTGGTG GTCCAGGTCA AGTGATTGAC      60

TTTACAGAAG ATAGCCAACC GGGTATGTCT GGTAATAATA GCCATACTAT TACAGAAGAT     120

TCTAAACCAA GTCAAGAGGA TGAGGTGATA ATCGGCGGTC AAGGTCAGGT GATTGACTTT     180

ACAGAAGATA CTCAATCTGG TATGTCTGGG GATAATAGCC ATACAGATGG GACAGTGCTT     240

GAAGAAGACT CTAAACCAAG TCAAGAGGAT GAGGTGATAA TCGGCGGTCA AGGTCAACTG     300

ATTGACTTTA CAGAAGATAC CCAAACCGGT ATGTCTGGG                            339
```

(2) INFORMATION FOR SEQ ID NO:4:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GAGGAAACTT TACCAACTGA ACAAGGCCAA TCTGGCTCTA CAACGGAGGT TGAGGATACT      60

AAAGGCCCAG AAGTCATTAT CGGCGGTCAG GGAGAGATTG TTGATATCGA GGAGAACTTA     120

CCAACTGAAC AAGGCCAATC TGGCTCTACA ACTGAAGTAG AGGATACTAA AGGCCCAGAA     180

GTCATTATCG GCGGTCAAGG AGAGGTTGTT GATATTGAGG AGAGCTTACC AACTGAACAA     240

GGCCAATCTG GCTCTACAAC TGAAGTAGAA GAT                                  273
```

(2) INFORMATION FOR SEQ ID NO:5:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Glu Asp Thr Gln Thr Ser Gln Glu Asp Ile Val Leu Gly Gly Pro Gly
1               5                   10                  15

Gln Val Ile Asp Phe Thr Glu Asp Ser Gln Pro Gly Met Ser Gly Asn
            20                  25                  30

Ser His Thr Ile Thr Glu Asp Ser Lys Pro Ser Gln Glu Asp Glu Val
        35                  40                  45

Ile Ile Gly Gly Gln Gly Gln Val Ile Asp Phe Thr Glu Asp Thr Gln
    50                  55                  60

Ser Gly Met Ser Gly Asp Asn Ser His Thr Asp Gly Thr Val Leu Glu
65                  70                  75                  80

Glu Asp Ser Lys Pro Ser Gln Glu Asp Glu Val Ile Ile Gly Gly Gln
                85                  90                  95

Gly Gln Val Ile Asp Phe Thr Glu Asp Thr Gln Thr Gly Met Ser Gly
            100                 105                 110
```

(2) INFORMATION FOR SEQ ID NO:6:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Glu Glu Thr Leu Pro Thr Glu Gln Gly Gln Ser Gly Ser Thr Thr Glu
1               5                   10                  15

Val Glu Asp Thr Lys Gly Pro Glu Val Ile Ile Gly Gly Gln Gly Glu
            20                  25                  30

Ile Val Asp Ile Glu Glu Asn Leu Pro Thr Glu Gln Gly Gln Ser Gly
        35                  40                  45

Ser Thr Thr Glu Val Glu Asp Thr Lys Gly Pro Glu Val Ile Ile Gly
```

```
                50                  55                  60
Gly Gln Gly Glu Val Val Asp Ile Glu Glu Ser Leu Pro Thr Glu Gln
 65                  70                  75                  80

Gly Gln Ser Gly Gly Ser Thr Thr Glu Val Glu Asp
                 85                  90
```

(2) INFORMATION FOR SEQ ID NO:7:

(i) SEQUENCE CHARACTERISTICS:
        (A) LENGTH: 158 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Glu Asp Thr Gln Thr Ser Gln Glu Asp Ile Val Leu Gly Gly Pro Gly
 1               5                  10                  15

Gln Val Ile Asp Phe Thr Glu Asp Ser Gln Pro Gly Met Ser Gly Asn
                 20                  25                  30

Asn Ser His Thr Thr Glu Asp Ser Lys Pro Ser Gln Glu Asp Glu Val
                 35                  40                  45

Ile Ile Gly Gly Gln Gly Gln Val Ile Asp Phe Thr Glu Asp Thr Gln
         50                  55                  60

Ser Gly Met Ser Gly Asp Asn Ser His Thr Asp Gly Thr Val Leu Glu
 65                  70                  75                  80

Glu Asp Ser Lys Pro Ser Gln Glu Asp Glu Val Ile Ile Gly Gly Gln
                 85                  90                  95

Gly Gln Val Ile Asp Phe Thr Glu Asp Thr Gln Thr Gly Met Ser Gly
                100                 105                 110

Ala Gly Gln Val Glu Ser Pro Thr Ile Thr Glu Thr His Lys Pro
                115                 120                 125

Glu Ile Ile Met Gly Gly Gln Ser Asp Pro Ile Asp Met Val Glu Asp
         130                 135                 140

Thr Leu Pro Gly Met Ser Gly Ser Asn Glu Ala Glu Asp Thr
145                 150                 155
```

(2) INFORMATION FOR SEQ ID NO:8:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Glu Glu Thr Leu Pro Thr Glu Gln Gly Gln Ser Gly Ser Thr Thr Glu
 1               5                  10                  15

Val Glu Asp Thr Lys Gly Pro Glu Val Ile Ile Gly Gly Gln Gly Glu
                 20                  25                  30

Ile Val Asp Ile Glu Glu Asn Leu Pro Thr Glu Gln Gly Gln Ser Gly
         35                  40                  45

Ser Thr Thr Glu Val Glu Asp Thr Lys Gly Pro Glu Val Ile Ile Gly
 50                  55                  60

Gly Gln Gly Glu Val Val Asp Ile Glu Glu Ser Leu Pro Thr Glu Gln
 65                  70                  75                  80
```

```
Gly Gln Ser Gly Ser Thr Thr Glu Val Glu Asp Ser Lys Pro Lys Leu
                85                  90                  95

Ser Ile His Phe Asp Asn Glu Trp Pro Lys Glu Asp
            100                 105
```

(2) INFORMATION FOR SEQ ID NO:9:

(i) SEQUENCE CHARACTERISTICS:
        (A) LENGTH: 1374 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1164

(xi) SEQUENCE DESCRIPTION: SEQ ID NO:9:

```
CTA GAT ACC TCA GAA AAC AAA AAA TCT GTA ACT GAA AAA GTA ATA ACT      48
Leu Asp Thr Ser Glu Asn Lys Lys Ser Val Thr Glu Lys Val Ile Thr
 1               5                  10                  15

AGC GAT GTT AAA TAT AAG ATT AAT GAT AAA GAA GTG AAA GGT AAA GAA      96
Ser Asp Val Lys Tyr Lys Ile Asn Asp Lys Glu Val Lys Gly Lys Glu
                20                  25                  30

CTA GAC GAT GTC TCT TTA ACT TAC AGT AAA GAA ACC GTT CGT AAG CCA     144
Leu Asp Asp Val Ser Leu Thr Tyr Ser Lys Glu Thr Val Arg Lys Pro
             35                  40                  45

CAG GTG GAA CCA AAT GTT CCT GAT ACA CCT CAG GAA AAA CCA TTG ACA     192
Gln Val Glu Pro Asn Val Pro Asp Thr Pro Gln Glu Lys Pro Leu Thr
         50                  55                  60

CCG CTT GCA CCG TCA GAA CCT TCA CAA CCA TCT ATT CCA GAG ACA CCA     240
Pro Leu Ala Pro Ser Glu Pro Ser Gln Pro Ser Ile Pro Glu Thr Pro
 65                  70                  75                  80

CTG ATA CCG TCA GAA CCT TCA GTT CCA GAG ACA TCA ACA CCA GAA GGT     288
Leu Ile Pro Ser Glu Pro Ser Val Pro Glu Thr Ser Thr Pro Glu Gly
                 85                  90                  95

CCA ACA GAG GGA GAA AAT AAT CTT GGT GGT CAG AGT GAA GAG ATA ACG     336
Pro Thr Glu Gly Glu Asn Asn Leu Gly Gly Gln Ser Glu Glu Ile Thr
                100                 105                 110

ATT ACA GAA GAT TCT CAA TCA GGG ATG TCT GGT CAA AAT CCT GGT TCT     384
Ile Thr Glu Asp Ser Gln Ser Gly Met Ser Gly Gln Asn Pro Gly Ser
            115                 120                 125

GGA AAT GAA ACA GTG GTT GAA GAC ACT CAA ACA AGT CAA GAG GAT ATT     432
Gly Asn Glu Thr Val Val Glu Asp Thr Gln Thr Ser Gln Glu Asp Ile
        130                 135                 140

GTA CTT GGT GGT CCA GGT CAA GTG ATT GAC TTT ACA GAA GAT AGC CAA     480
Val Leu Gly Gly Pro Gly Gln Val Ile Asp Phe Thr Glu Asp Ser Gln
145                 150                 155                 160

CCG GGT ATG TCT GGT AAT AAT AGC CAT ACT ATT ACA GAA GAT TCT AAA     528
Pro Gly Met Ser Gly Asn Asn Ser His Thr Ile Thr Glu Asp Ser Lys
                165                 170                 175

CCA AGT CAA GAG GAT GAG GTG ATA ATC GGC GGT CAA GGT CAG GTG ATT     576
Pro Ser Gln Glu Asp Glu Val Ile Ile Gly Gly Gln Gly Gln Val Ile
            180                 185                 190

GAC TTT ACA GAA GAT ACT CAA TCT GGT ATG TCT GGG GAT AAT AGC CAT     624
Asp Phe Thr Glu Asp Thr Gln Ser Gly Met Ser Gly Asp Asn Ser His
        195                 200                 205

ACA GAT GGG ACA GTG CTT GAA GAA GAC TCT AAA CCA AGT CAA GAG GAT     672
Thr Asp Gly Thr Val Leu Glu Glu Asp Ser Lys Pro Ser Gln Glu Asp
    210                 215                 220
```

-continued

```
GAG GTG ATA ATC GGC GGT CAA GGT CAA GTG ATT GAC TTT ACA GAA GAT      720
Glu Val Ile Ile Gly Gly Gln Gly Gln Val Ile Asp Phe Thr Glu Asp
225                 230                 235                 240

ACC CAA ACC GGT ATG TCT GGG GCT GGA CAA GTA GAG AGT CCA ACA ATC      768
Thr Gln Thr Gly Met Ser Gly Ala Gly Gln Val Glu Ser Pro Thr Ile
                245                 250                 255

ACC GAA GAA ACC CAT AAA CCA GAA ATA ATC ATG GGC GGT CAA AGT GAC      816
Thr Glu Glu Thr His Lys Pro Glu Ile Ile Met Gly Gly Gln Ser Asp
            260                 265                 270

CCT ATT GAT ATG GTT GAG GAC ACT CTT CCT GGT ATG TCT GGC TCT AAT      864
Pro Ile Asp Met Val Glu Asp Thr Leu Pro Gly Met Ser Gly Ser Asn
        275                 280                 285

GAA GCT ACT GTT GTG GAA GAA GAC ACA CGT CCT AAA CTT CAA TTC CAT      912
Glu Ala Thr Val Val Glu Glu Asp Thr Arg Pro Lys Leu Gln Phe His
    290                 295                 300

TTT GAT AAT GAA GAG CCC GTT CCT GCA ACG GTT CCA ACC GTT TCT CAA      960
Phe Asp Asn Glu Glu Pro Val Pro Ala Thr Val Pro Thr Val Ser Gln
305                 310                 315                 320

ACT CCT ATT GCT CAG GTA GAA AGT AAA GTG CCT CAT GCC AAA GCA GAG     1008
Thr Pro Ile Ala Gln Val Glu Ser Lys Val Pro His Ala Lys Ala Glu
                325                 330                 335

AGT GCG TTA CCT CAA ACT GGA GAT ACA AAT AAA CTA GAA ACG TTC TTT     1056
Ser Ala Leu Pro Gln Thr Gly Asp Thr Asn Lys Leu Glu Thr Phe Phe
            340                 345                 350

ACC ATT ACA GCA CTA ACT GTT ATT GGA GCG GCA GGA TTA CTA GGC AAA     1104
Thr Ile Thr Ala Leu Thr Val Ile Gly Ala Ala Gly Leu Leu Gly Lys
        355                 360                 365

AAA CGT CGT AAT AAT CAA ACT GAT TAA TCA GCA GAT TTC ATC AAA CGC     1152
Lys Arg Arg Asn Asn Gln Thr Asp  *  Ser Ala Asp Phe Ile Lys Arg
    370                 375                 380

TAT AAA CAA GGC TAACATTTTA GCCTTGTTTT ATATTGTTTC ACTGACCTCT         1204
Tyr Lys Gln Gly
385

AAAAGTTATG ACTGTTTTAA AGGGGGGGTA GGCCAATCCT CAAAAGTAGT TAAGTTGAGA   1264

AACACCACAT CACTTTAGTC TTACTGCGCA TACTAAAAGC AAAAGATAAT TAGGAGCAGT   1324

TGCTAACTGG AAAAAATCAA ATGCAAAGCT AGTTGCCAAA GAACTCTAGA             1374
```

(2) INFORMATION FOR SEQ ID NO:10:

(i) SEQUENCE CHARACTERISTICS:
        (A) LENGTH: 840 base pairs
        (B) TYPE: nucleic acid
        (C) STRANDEDNESS: single
        (D) TOPOLOGY: linear (ii) MOLECULE TYPE: protein (ix) FEATURE:
        (A) NAME/KEY: CDS
        (B) LOCATION: 1..840

(xi) SEQUENCE DESCRIPTION: SEQ ID NO:10:

```
CTC GAG GAA ACT TTG CCA ACA GAG GAA CAT CAA TCA GGT GAT ACC ACA       48
Leu Glu Glu Thr Leu Pro Thr Glu Glu His Gln Ser Gly Asp Thr Thr
390                 395                 400

ACT ATT GAA GAT ACT CGC CCG ATT GAT ACC ATG TCA GGT CTA TCA GGA       96
Thr Ile Glu Asp Thr Arg Pro Ile Asp Thr Met Ser Gly Leu Ser Gly
405                 410                 415                 420

GAG ACT GGG CAG TCT GGT AAT ACT ACA ATT GAG GAA GAT AGT ACG ACT      144
Glu Thr Gly Gln Ser Gly Asn Thr Thr Ile Glu Glu Asp Ser Thr Thr
                425                 430                 435
```

-continued

```
CAC GTT AAA TTC TCA AAA CGT GAT ATT AAT GGT AAA GAA CTA GCA GGT      192
His Val Lys Phe Ser Lys Arg Asp Ile Asn Gly Lys Glu Leu Ala Gly
            440                 445                 450

GCT ATG ATT GAA CTA CGT AAT CTA TCA GGT CAA ACT ATT CAA TCA TGG      240
Ala Met Ile Glu Leu Arg Asn Leu Ser Gly Gln Thr Ile Gln Ser Trp
            455                 460                 465

ATA TCA GAC GGC ACA GTT AAA GTT TTC TAC TTG ATG CCA GGG ACT TAT      288
Ile Ser Asp Gly Thr Val Lys Val Phe Tyr Leu Met Pro Gly Thr Tyr
    470                 475                 480

CAA TTT GTG GAG ACG GCA GCG CCA GAA GGT TAT GAA TTG GCA GCT CCA      336
Gln Phe Val Glu Thr Ala Ala Pro Glu Gly Tyr Glu Leu Ala Ala Pro
485                 490                 495                 500

ATT ACC TTC ACA ATT GAT GAG AAA GGA CAA ATT TGG GTA GAC AGT ACA      384
Ile Thr Phe Thr Ile Asp Glu Lys Gly Gln Ile Trp Val Asp Ser Thr
            505                 510                 515

ATT ACT GAG GCG AGT CAA TCT ATT GAT TTC GAG GAA ACT TTA CCA ACT      432
Ile Thr Glu Ala Ser Gln Ser Ile Asp Phe Glu Glu Thr Leu Pro Thr
            520                 525                 530

GAA CAA GGC CAA TCT GGC TCT ACA ACG GAG GTT GAG GAT ACT AAA GGC      480
Glu Gln Gly Gln Ser Gly Ser Thr Thr Glu Val Glu Asp Thr Lys Gly
            535                 540                 545

CCA GAA GTC ATT ATC GGC GGT CAG GGA GAG ATT GTT GAT ATC GAG GAG      528
Pro Glu Val Ile Ile Gly Gly Gln Gly Glu Ile Val Asp Ile Glu Glu
            550                 555                 560

AAC TTA CCA ACT GAA CAA GGC CAA TCT GGC TCT ACA ACT GAA GTA GAG      576
Asn Leu Pro Thr Glu Gln Gly Gln Ser Gly Ser Thr Thr Glu Val Glu
565                 570                 575                 580

GAT ACT AAA GGC CCA GAA GTC ATT ATC GGC GGT CAA GGA GAG GTT GTT      624
Asp Thr Lys Gly Pro Glu Val Ile Ile Gly Gly Gln Gly Glu Val Val
            585                 590                 595

GAT ATT GAG GAG AGC TTA CCA ACT GAA CAA GGC CAA TCT GGC TCT ACA      672
Asp Ile Glu Glu Ser Leu Pro Thr Glu Gln Gly Gln Ser Gly Ser Thr
            600                 605                 610

ACT GAA GTA GAA GAT AGC AAG CCT AAA CTC TCT ATC CAC TTT GAT AAC      720
Thr Glu Val Glu Asp Ser Lys Pro Lys Leu Ser Ile His Phe Asp Asn
            615                 620                 625

GAG TGG CCT AAG GAA GAC AAA CCA CAA CTA CCT GCC GTT GAA AAA CCT      768
Glu Trp Pro Lys Glu Asp Lys Pro Gln Leu Pro Ala Val Glu Lys Pro
            630                 635                 640

AAG ACT AAG GAG AGC TTG CCA GCC GCA GGG GAA GCT GAA CAT GTC TTA      816
Lys Thr Lys Glu Ser Leu Pro Ala Ala Gly Glu Ala Glu His Val Leu
645                 650                 655                 660

TCT ACT ATC GTG GGA GCA ATG ATC                                      840
Ser Thr Ile Val Gly Ala Met Ile
            665
```